US012605481B2

(12) United States Patent
Okamoto et al.

(10) Patent No.: US 12,605,481 B2
(45) Date of Patent: Apr. 21, 2026

(54) ADHESION PREVENTING MATERIAL FOR OPHTHALMIC APPLICATIONS, AND METHOD FOR PRODUCING SAME

(71) Applicant: BMG Incorporated, Kyoto (JP)

(72) Inventors: Yoshifumi Okamoto, Tsukuba-city (JP); Sujin Hoshi, Tsukuba-city (JP); Fumiki Okamoto, Tokyo (JP); Mikki Arai, Fukuoka-city (JP); Shuhei Tanida, Kizugawa-city (JP); Yusuke Kojitani, Kyoto-city (JP); Motoki Fujimura, Kyoto-city (JP); Woogi Hyon, Kyoto-city (JP); Suong-Hyu Hyon, Uji-city (JP)

(73) Assignee: BMG Incorporated, Kyoto (JP)

( * ) Notice: Subject to any disclaimer, the term of this patent is extended or adjusted under 35 U.S.C. 154(b) by 150 days.

(21) Appl. No.: 18/699,326

(22) PCT Filed: Mar. 31, 2022

(86) PCT No.: PCT/JP2022/016784
§ 371 (c)(1),
(2) Date: Apr. 8, 2024

(87) PCT Pub. No.: WO2023/067830
PCT Pub. Date: Apr. 27, 2023

(65) Prior Publication Data
US 2025/0235579 A1 Jul. 24, 2025

(30) Foreign Application Priority Data
Oct. 20, 2021 (JP) ................................. 2021-171681

(51) Int. Cl.
A61L 24/10 (2006.01)
A61L 24/00 (2006.01)
A61L 24/08 (2006.01)

(52) U.S. Cl.
CPC ......... *A61L 24/108* (2013.01); *A61L 24/0036* (2013.01); *A61L 24/08* (2013.01); *A61L 2430/16* (2013.01)

(58) Field of Classification Search
None
See application file for complete search history.

(56) References Cited

U.S. PATENT DOCUMENTS

2022/0016311 A1* 1/2022 Tanida .................... A61L 15/64

FOREIGN PATENT DOCUMENTS

JP 2018-039886 3/2018
JP 2019-092645 6/2019
(Continued)

OTHER PUBLICATIONS

International Search Report and Written Opinion for International Application No. PCT/JP2022/016784 mailed on Jun. 14, 2022, 8 pgs.
(Continued)

*Primary Examiner* — Dominic Lazaro
(74) *Attorney, Agent, or Firm* — Amin, Turocy & Watson, LLP

(57) ABSTRACT

In specific embodiments, provided is a material for preventing adhesion of membranes in an ophthalmic surgery for treatment of glaucoma or the like without using mitomycin-C or the like. Particularly provided is such material, which is easy to handle and has no risk of histolysis or infections. In a production method of a preferred embodiment, prepared are: aldehyde-modified dextran (first reactant) having weight-average molecular weight of 10,000-5,000,000 and introduced aldehyde group-per-anhydrous glucose unit (mol/AGU) of 0.4-0.7; and succinic anhydride-added poly-L-lysine (second reactant) having weight-average molecular weight of 1000-100,000 and having residual
(Continued)

Create a new channel for the aqueous humor to reach below the conjunctiva (white of the eye)

Before the surgery
Places where aqueous humor is difficult to flow

Surgery method
Adhesion preventing material
Pleural flap

After the surgery
Conjunctiva
Adhesion preventing material

Aqueous humor collects under the conjunctiva amino group ratio of 80-99%; then, they are mixed together so that aldehyde group-to-amino group molar ratio becomes 0.9-1.1 and are reacted in presence of water so that polymer concentration becomes 8-20%; and a hydrogel produced by the reaction, or a suspension before gelation, is freeze-dried to produce a porous sheet having a thickness of 0.1-0.8 mm.

5 Claims, 9 Drawing Sheets

(56)                     References Cited

FOREIGN PATENT DOCUMENTS

| WO | 2006080523 | 8/2006 | |
| WO | 2008066182 | 6/2008 | |
| WO | 2020122007 | 6/2020 | |
| WO | WO-2020122007 A1 * | 6/2020 | ............ A61L 15/26 |

OTHER PUBLICATIONS

Tanito et al, Subconjunctival implantation of ologen Collagen Matrix to treat ocular hypotony after filtration glaucoma surgery, Eye (2017) 31, 1475-1479.
Tsurumaru et al, Seprafi Im as a New Antifi brotic Agent Following Trabeculectomy in Rabbit Eyes, Department of Ophthalmology, Kurume University School of Medicine,Kurume, Fukuoka, Japan, Jpn J Ophthalmol 2009;53:164-170.
Okomoto et al, Effect of Intraoperative Application of LYDEX for Trabeculectomy of Eye of Domestic Rabbit, Journal Japanese Ophthalmological Society vol. 120 issued on Mar. 2, 2016.

* cited by examiner

Sheet-shaped "LYDEX"™

Create a new channel for the aqueous humor to reach below the conjunctiva (white of the eye)

At end of the surgery

Four weeks after the surgery

Four months after the surgery

Intraocular pressure (mmHg)

Having an intraocular pressure-lowering effect for at least 4 months after the surgery Tissue section, four months after the surgery Remaining for at least 4 months after the surgery
No obvious inflammation or tissue destruction

ADHESION PREVENTING MATERIAL FOR OPHTHALMIC APPLICATIONS, AND METHOD FOR PRODUCING SAME

TECHNICAL FIELD

The present invention is directed to an adhesion preventing material, which is formed of a hydrogel (water-containing polymer gel) having low toxicity and moderate durability against decomposition, and is used for preventing adhesion, or for securing a space, between the conjunctiva and sclera, fusion between scleras, or between other ophthalmological biological membranes. The present invention is especially directed to a glaucoma surgical aid that utilizes the adhesion preventing and adhesive (sticky) effects of hydrogels with low cytotoxicity.

BACKGROUND TECHNOLOGY

Glaucoma is a disease that causes characteristic changes in the optic nerve and visual field, and is characterized by functional and structural abnormalities of the eyes, which may be ameliorated or suppressed by sufficiently lowering intraocular pressure (the pressure of the aqueous humor inside the cornea). Treatment is necessary to prevent the progression of visual-field narrowing due to glaucoma and the resulting blindness. The inside of the eyeball is filled with vitreous humor and aqueous humor, and the volume of the vitreous body hardly changes while aqueous humor is constantly produced from the ciliary body that surrounds the crystalline lens, and is drained to the outside of the eyeball through Schlemm's canals that are distributed around the cornea. Intraocular pressure is maintained through balancing between production and drainage of the aqueous humor whereas, if the drainage channels such as Schlemm's canal become clogged for some reason (mainly aging), the balance of intraocular pressure would be disrupted, leading to progression of visual-field impairment.

Major therapeutic approaches to glaucoma are administration of eye drops and surgery. Eye drops decrease the intraocular pressure by suppressing production of aqueous humor, or decreasing the outflow resistance during drainage of aqueous humor so as to promote its drainage. When the intraocular pressure would not be sufficiently lowered with drug therapy such as eye drops or with laser treatment, or when visual field deterioration would not be stopped even after the intraocular pressure has been lowered, surgeries (trabeculectomy, filtration glaucoma surgery) of newly creating an outlet (drainage channel) for the aqueous humor from the eyeball are performed.

Specifically, the sclera surrounding the eyeball and the tissues (trabecular meshwork) at inside of the eyeball are excised at a location adjacent to the cornea to create a drainage channel. In such occasions, it is necessary to allow the aqueous humor to leak out little by little to prevent the intraocular pressure from decreasing excessively and from making the eyeball too soft; and thus, suturing is made in a manner that the drainage channel is covered with a scleral flap. Meanwhile, covering the region including the scleral flap by the conjunctiva would cause adhering between the conjunctiva and the sclera and between the scleras, at a location of the drainage channel, resulting in blockage of the drainage channel and hindering of the decreasing of intraocular pressure. In order to prevent adhesion of these wounds and secure the outflow path for aqueous humor, mitomycin C (MMC) has been applied as spread to the conjunctiva and sclera at this location.

Nevertheless, mitomycin C is difficult to handle and may cause histolysis and thus cause infection. Mitomycin C is an anticancer drug and has a strong fibroblast proliferation inhibitory effect. If the action and effect of mitomycin C is too strong, such as when the concentration of mitomycin C administered is too high, the conjunctiva and sclera may cause histolysis; and thus, the tissue around the drainage channel may become thinner and a hole may be formed. This leads to an abnormal drop in intraocular pressure, which has an adverse effect on visual function, and may also lead to infections such as endophthalmitis that can lead to blindness. Conversely, if the action and effect of mitomycin C are too weak, the scleral flap will adhere to the inner scleral part and the conjunctiva that covers the scleral flap, which will also block the drainage channel created by the resection so that effect of the surgery will be lost.

There has been a study report on using Seprafilm (registered trademark; a mixture of sodium hyaluronate and carboxymethylcellulose) in glaucoma surgery, as diverted from being widely used as adhesion preventing material in intraperitoneal surgery (Non-Patent Document 1). Although the inflammation is slight, the long-term effects are unknown because the film is absorbed within a month after surgery. Attempts have also been made to use trehalose or hyaluronic acid sheets, but these also disappear approximately one month after surgery, and their retaining period in the body is too short, so neither has been put to practical use. Meanwhile, in order to prevent an excessive decrease in intraocular pressure, there has been an attempt to insert a collagen matrix (Non-Patent Document 2).

Meanwhile, there have been two-reactant adhesive and hydrogel-forming material (LYDEX; registered trademark), which is proposed by BMG Co., Ltd. and comprises powder mixture of aldehyde glucan and modified poly-L-lysine and which have low toxicity and decomposition rate of which in living body is freely controllable (Patent Documents 1 and 2). The two-reactant type hydrogel-forming material (LYDEX; registered trademark) comprises first and second reactants, which are respectively made from dextran having been commonly used as a medical material and polylysine that is a food additive, as starting materials. Therefore, the hydrogel obtained from this is expected to be safe for the human body and to suppress the occurrence of serious complications. Meanwhile, according to claim 7 of Patent Document 2, this hydrogel is assumed to "changes into a sol state by self-decomposition after a gel-state retaining period that is able to be arbitrarily set between one day and one month."

PRIOR ART DOCUMENTS

Patent Documents

Patent Document 1: WO2008/066182 (JP4571693B)
Patent Document 2: WO2006/080523 (JP4092512B)

Non-Patent Documents

Non-patent document 1: Tsurumaru N, Arai M, Teruya K, Sueda J, Yamakawa R., "Seprafilm as a new antifibrotic agent following trabeculectomy in rabbit eyes." Jpn J Ophthalmol.; 53(2):164-70 (2009 March). doi: 10.1007/s10384-008-0638-3. Epub 2009 Mar. 31.
Non-patent document 2: https://www.nature.com/articles/eye201798, M Tanito, A Okada, Y Mori, I Sano, Y Ikeda and E Fujihara, "Subconjunctival implantation of ologen Collagen Matrix to treat ocular hypotony after filtration glaucoma surgery," Eye (2017) 31, 1475-1479.

OUTLINE OF THE INVENTION

Problems to be Solved by the Invention

In view of the above, the present invention aims to provide a material and method for preventing adhesions around the aqueous humor drainage channel during ophthalmic surgery such as glaucoma treatment without using drugs such as mitomycin C that make it difficult for wounds to heal. In particular, it is aimed to provide those that are easy to handle and have no risk of histolysis or infection.

The inventors have modified a type of the LYDEX products having conventionally been mainly used and produced, which had been assumed to be disintegrated within a relatively short period of time, so as to retain the hydrogel state for at least four months, and preferably for six months to one year. Then, such LYDEX product capable of retaining the hydrogel state for long or midterm period, has been attempted to be used to prevent adhesions in extremely small areas during ophthalmic surgery.

The inventors, in course of intensive study, have produced a hydrogel sheet from the LYDEX products under specific conditions, and then freeze-dry the hydrogel sheet to create a porous sheet in a specific state (appropriately referred to as "sponge type LYDEX") Then, during the above-mentioned glaucoma surgery, a small piece cut out from the porous sheet was placed as interposed between the conjunctiva and the sclera, in vicinity of the scleral flap covering the drainage port. As a result, the adhesion-preventing effect was observed for at least four months. Moreover, the hydrogel produced from the "sponge type LYDEX" has moderate stickiness, and thus is advantageous in gradually causing water leakage while making it sticky while sticking the conjunctiva and sclera in vicinity of trabeculectomy and scleral flap site (the above drainage port).

Means to Solve the Problems

According to the production method in a preferred embodiment, prepared are: an aldehyde dextran (the first reactant) having a weight average molecular weight of 10,000 to 5,000,000 and aldehyde groups per anhydro glucose unit (mol/AGU) of 0.4 to 0.7; and succinic anhydride-added poly-L-lysine (second reactant) having a weight average molecular weight of 1,000 to 100,000 and a residual amino-group ratio of 80 to 99%. Then, the first and second reactants are mixed so that the reaction molar ratio of aldehyde groups-to-amino groups becomes 0.9 to 1.1; and are then reacted with each other in presence of water where concentration of the polymer becomes 8 to 20%. Subsequently, hydrogel obtained by the reaction, or suspension before the gelation, are freeze-dried to a porous sheet having a thickness of 0.1 to 0.8 mm.

In a preferred embodiment, freeze-drying is made as follows: a mixed aqueous solution or suspension of the first and second reactants is prepared and then stored for 1 to 3 hours for example under refrigeration (at 3° C. to 6° C. for example); then, rapidly cooled to −10° C. or lower, particularly to −20° C. or lower so as to be frozen; and subsequently, is submitted to depressurizing while temperature around the vacuum container is kept at 25° C. to 30° C. for example.

In a preferred embodiment, a moisture-retaining plasticizer formed of glycerin or other water-soluble low-molecular compound is added at a time the hydrogel is formed by a reaction between the first and second reactants, by an amount of 30 to 100% or 50 to 90% by weight based on total weight of the first and second reactants.

In a preferred embodiment, the obtained porous sheet has substantially no large voids, such as having a long axis diameter of 80 μm or more, 50 μm or more, or 30 μm or more when a surface or a cut surface is observed with a stereomicroscope. Even when such large voids are existed, number of them per square centimeter is no more than 5, no more than 3, or no more than 1, for example.

In a preferred embodiment, the porous sheet obtained has an apparent density (bulk density) of 0.1 to 0.25 g/cm$^3$.

In a preferred embodiment, adhesion preventing material for ophthalmology, which is a continuous-pore porous sheet comprising a resin material formed by reaction product of: (1) an aldehyde glycan as a first reactant having a weight average molecular weight of 10,000 to 5,000,000, and having an aldehyde group introduction amount per anhydroglucose unit (mol/AGU) of 0.4 to 0.7; and (2) acid anhydride-added poly-L-lysine having a weight average molecular weight of 1,000 to 100,000 and a residual amino-group percentage of 80 to 99%; where (3) an aldehyde group-to-amino group reaction molar ratio is 0.9 to 1.1. (4) apparent density (bulk density) is 0.1 to 0.25 g/cm$^3$, and (5) thickness is 0.1 to 0.8 mm.

Advantages of the Invention

When such obtained porous sheet is used so as to prevent adhesions during ophthalmic surgery, the solid form of the hydrogel will be maintained for a period of 4 months or more (medium-to-long term) in a manner to prevent adhesions. The hydrogel has low toxicity and irritation to cells and tissues, that may cause slight inflammation if any, so that adhesion would be hard to progress. In particular, when used as an auxiliary material for glaucoma surgery, the hydrogel not only prevents the aqueous humor drainage channel from being blocked by adhesions, but also allows the aqueous humor to drain through the holes so that long-term reduction in intraocular pressure is expected.

EMBODIMENTS FOR CARRYING OUT THE INVENTION

Figure 1:
FIG. 1 shows a photograph showing appearances of the obtained porous sheets ("sponge type LYDEX").

The adhesion-preventing material for ophthalmology of the present invention is produced by freeze-drying a hydrogel obtained from a two-reactant adhesive as described in WO2008/066182 (Patent Document 1) or WO2006/080523 (Patent Document 2) so as to obtain a porous material. Namely, a two-reactant adhesive in the form of a mixed powder or two liquids is converted into a hydrogel, through a state of a mixed aqueous solution, and then made into a porous material by a drying method such as freeze-drying that achieves fine porosity.

The shape of the porous material here may be granular, string-shaped, net-shaped, etc., but is preferably a sheet-shaped one or a porous sheet, from viewpoints of ease of manufacture and convenience during ophthalmic surgery. For such porous sheet, the mixed aqueous solution of a two-reactant adhesive is spread to a thin and uniform thickness (0.3 to 1 mm for example), and then freeze-dried immediately or after a short time of natural drying (diffusion of moisture into indoor air). For example, the freeze-drying may be performed by rapidly cooling to −5 to −40° C. or −10 to −30° C. and then dried under reduced pressure, at 50 to 500 hectopascals for example. Meanwhile, when using the porous sheet, the sheet may be cut into appropriate size in length and width as depending on the size of the scleral flap to be formed during ophthalmic surgery. Instead of this, flake-shaped or granular porous bodies may be produced by using an agitation-type freeze-drying device, and be used as are, or after being split or trimmed as appropriately.

The above-mentioned two-reactant adhesive is formed by a first reactant made of aldehyde glycan and a second reactant made of carboxylic anhydride-added (partially carboxylated) poly-L-lysine. The first and second reactants are produced in the form of an aqueous solution for the alde-hydation and the partial carboxylation, but the solution may be converted to powders by freeze-drying, etc., and then, in particular, made into powder mixture containing the first and second reactants in an appropriate molar ratio. The mixed aqueous solution containing the first and second reactants in an appropriate molar ratio for obtaining the hydrogel may be obtained by mixing two-liquid two-reactant adhesive, namely by mixing aqueous solutions of the first and second reactants, and may also be obtained by dissolving the above mixed powder in water.

Aldehyde glycan as the first reactant is produced by oxidizing water-soluble or water-dispersible polysaccha-rides such as glucans (polymers of D-glucose) with periodic acid or periodate salts so as to introduce 0.4 to 1.0 aldehyde groups, particularly 0.4 to 0.8 or 0.4 to 0.7 aldehyde groups, per anhydro-glucose unit. The glycan here is in one pre-ferred embodiment α-glucan, for example dextran or dex-trin. Glycans (polysaccharides) may be glycosaminoglycans such as hyaluronic acid, guar gum, locust bean gum, carra-geenan, hydroxyl-propyl methylcellulose, hydroxyl-propyl cellulose, and the like. The weight average molecular weight (e.g., by SEC-MALLS method using DMSO solvent) of the aldehyde glycans may be in a range from 10,000 to 5,000,000, particularly in a range from 20,000 to 500,000 or from 20,000 to 200,000.

Partially carboxylated poly-L-lysine as the second reac-tant is produced from poly-L-lysine having a weight average molecular weight of 1,000 to 1,000,000 or 2,000 to 100,000, by reacting its amino groups (mainly side chain amino groups) with a carboxylic acid anhydride such as succinic anhydride, especially with a dicarboxylic acid anhydride. In particular, the residual amino group ratio (percentage) is 70 to 95% or 75 to 95%, especially 80 to 95%. As the carboxylic acid anhydride other than the succinic anhydride, glutaric anhydride, malic anhydride, etc. may also be used depending on the occasions. Meanwhile, the molar ratio of aldehyde groups-to-amino groups in the mixed aqueous solution for forming the hydrogel may preferably be around 1, that is, 0.8 to 1.3, 0.9 to 1.2, or 0.9 to 1.1.

When the hydrogel obtained by using the two-reactant adhesive described above is kept in a saturated state of water at a temperature similar to that of a living body, the period until the gel disintegrates is 4 months or more, 6 months or more, one year to 1.5 years, or one to two years.

When to use the mixed powder to form the hydrogel, the mixed powder is preferably made of, for example, porous bodies, which has random shapes (shapes far from a sphere), and has the average particle size (average length of biaxial average diameters by image analysis) of 10 to 150 μm where water content of the mixed powder is kept at 2.0% or less. When such mixed powder is dissolved in water, the hydrogel having high strength is quickly obtainable while forming an appropriate microscopically heterogeneous structure.

As mentioned above, the mixed aqueous solution for forming the hydrogel may contain a moisture-retaining plasticizer such as glycerin. The amount of the moisturizing plasticizer added may be, for example, 30 to 100% by weight, 40 to 90% by weight, or 50 to 80% by weight, based on the total weight of the first and second reactants. In addition to glycerin, moisturizing plasticizers that can be added include propylene glycol, 1,3-butylene glycol, 1,2-pentanediol, 1,2-hexanediol, polyethylene glycol, sorbitol, maltitol, dl-pyrrolidone, sodium carboxylate, sodium lac-tate, polyglycerin, sodium hyaluronate and trimethylglycine. These moisturizing ingredients can be added, for example, by mixing them into the mixed powder of the two-reactant adhesive.

To form the hydrogel, the ratio (concentration) of the total weight of the first and second reactants to the weight of the mixed aqueous solution is preferably 8 to 20% or 10 to 15%. If this concentration is, for example, 5% or less, it is unable to make the diameter of the voids as uniform, and the above-mentioned large voids may occur in a porous material such as a porous sheet. If there are large voids for example, the strength of the hydrogel after one month of being implanted in a living body may be decreased, and the adhesion prevention performance may be adversely affected.

The resulting porous material may have an apparent density (bulk density) of 0.1 to 0.25 g/cm$^3$. Tis range is preferred because gel strength is maintained over a long period of time in living body and the hydrogel is easily manufacturable.

EXAMPLES

Hereinafter, embodiments of the present invention will be described with reference to Examples, but these are not intended to limit the scope of the present invention.

Example 1

A porous sheet was produced as follows and used in the above-mentioned glaucoma surgery.

1) Production of Aldehyde Dextran Aqueous Solution (ADaq)

Dextran 70 (Meito Sangyo Co., Ltd.) having a molecular weight of 70,000 is added to "water for injection" (WFI) and stirred at 50° C. for 30 min and at 280 rpm to be completely dissolved. Sodium metaperiodate (NaIO₄) is similarly added to the water for injection (WFI) and stirred and shaken at 50° C. for 10 min so as to be completely dissolved. At this time, the amount of aldehyde groups introduced into dextran may be changed by arbitrarily adjusting the ratio of added NaIO₄ to Dextran 70 (NaIO₄/Dex70 ratio). Thus obtained aqueous solutions of Dextran 70 aqueous solution and NaIO₄ were stirred as mixed at 50° C. for 3 hours and at 280 rpm to obtain a reaction solution. This reaction solution was placed in a cellulose tube (molecular weight cut off: 12,000-14,000) and dialyzed against room temperature tap water for 70 hours, and then against ion-exchanged water for 4 times for 45 minutes to remove iodine and sodium. The dialysate was filtered to remove dust by using a hydrophilic PTFE membrane filter with a pore size (φ) of 0.45 μm. The filtrate was dried with warm air at 40° C. for 20 hours or longer while shaking, and after turning the concentrate upside down, it was similarly dried with warm air at 40° C. for 20 hours or more. The concentrate thus obtained was dried under reduced pressure at room temperature for 15 hours or more to obtain a dried product. The dried product thus obtained was roughly crushed by hand into chunks of several centimeters, and then was crushed using a small hammer mill type crusher (Wonder Crush Mill D3V-10, Osaka Chemical Co., Ltd.). Fine pulverization was performed at a mesh-opening diameter (φ) of 0.5 mm and a rotation speed of 10,000 rpm. The finely ground product was dried under reduced pressure at 50° C. for 15 hours to obtain a powder of aldehyde dextran (AD), which is the first reactant.

As shown at the bottom of Table 1 below, the charging ratio (NaIO₄/Dextran 70) during such aldehyde conversion was set to 5.0/10. The amount of introduced aldehyde group (mol/AGU) achieved was 0.44 to 0.48 according to titration using a sodium thiosulfate-sulfuric acid system and a starch reagent. As shown in Table 1, as a comparative or reference example, one in which the amount of aldehyde groups introduced (mol/AGU) was smaller was also produced.

TABLE 1

| An example of the NaIO₄/Dextran 70 ratio of AD powder and the amount of aldehyde groups introduced | |
|---|---|
| Charge ratio of NaIO₄/Dextran 70 | Amount of aldehyde group introduced (mol/AGU) |
| 2.5/10 | 0.25~0.27 |
| 4.0/10 | 0.36~0.40 |
| 5.0/10 | 0.44~0.48 |

The aldehyde dextran (AD) powder thus obtained was placed into water for injection (WFI) to a concentration of 0.5 to 10% by weight, allowed to stand still, and kept under refrigeration (3 to 6° C.) so as to be swollen. This aldehyde-dextran (AD) swollen product was stirred in a 50° C. hot bath to be completely dissolved. Thus obtained aqueous solution was sterilized by filtration using a polyether sulfone (PES) syringe filter with a pore size (φ) of 0.22 μm to obtain a first reactant aqueous solution (ADaq).

2) Production of Succinic Anhydride-Treated Polylysine Aqueous Solution (SAPLaq)

Succinic anhydride was added to a 25% solution of polylysine (molecular weight 4,000, Chisso Corporation) and stirred at 50° C. for 1 hour so as to be reacted. Thereafter, water for injection (WFI) was added until the product reached a predetermined concentration; and after stirring gently, the mixture was sterilized by filtration using a PES syringe filter with a pore size (φ) of 0.22 μm so as to obtain a second reactant aqueous solution (APLaq). The SA/PL (succinic anhydride-to-polylysine) charging ratio "1.0/10" in the middle row of Table 2 below is directed to an Example of the embodiment, and the upper and lower rows are directed to comparative or reference examples.

TABLE 2

| An example of SAPL concentration of SAPLaq and SA/PL ratio | | | | | |
|---|---|---|---|---|---|
| 25% PL (%) | SA (%) | WFI (%) | SAPL concentration (%) | SA/PL ratio | Residual amino group ratio (%) |
| 20.0 | 0.5 | 79.5 | 0.5 | 1.0/10 | 81~93 |
| 40.0 | 1.0 | 59.0 | 10.0 | 1.0/10 | 81~93 |
| 40.0 | 2.0 | 58.0 | 10.0 | 2.0/10 | N/A |

Here, the residual percentage of free amino groups (side chain and terminal amino groups not involved in the formation of peptide bonds) (remaining amino group ratio) was determined as follows. First, after dissolving in water, a ninhydrin solution and an acetic acid/sodium acetate buffer solution of pH 5.5 were added, heated in a boiling water bath for 3 minutes, and then rapidly cooled to obtain a sample solution. Then, a test was conducted using the ultraviolet-visible absorbance measurement method of the Japanese Pharmacopoeia, and the absorbance at a wavelength of 570 nm was measured.

3) Production of Porous Sheet ("Sponge Type LYDEX") from Two Types of Aqueous Solutions Into a tray-shaped container made entirely of soft silicone, above-mentioned aqueous solutions of the first reactant and the second reactant (ADaq; SAPLaq), and distilled water (DW) were added and mixed quickly, and then left at room temperature (25° C.) for 10 min so as to obtain a suspension of the two-reactant adhesive (LYDEX suspension). Here, the distilled water (DW) was added so that the concentration of the two-reactant adhesive (SAPL concentration in Table 2) was a predetermined value in a range of 0.5 to 10%, and so as to be with uniform height (depth) of 0.7 mm in the tray-shaped container. Further, the reaction molar ratio of aldehyde group-to-amino group was set to 1.0.

Thus-obtained two-reactant adhesive suspension (LYDEX suspension) was stored at 5° C. for 2 hours, then quickly cooled to −25° C. so as to be completely frozen. Subsequently, frozen suspension of "LYDEX (registered trademark)" was allowed to stand still and dried under reduced pressure while maintaining at room temperature '25° C.) to 30° C. as the ambient temperature. That is, by sublimating and removing water, a sheet-like dried product with a thickness of 0.4 mm was obtained. Such a dried product will be referred to as "sponge type LYDEX" (LYDEX is a registered trademark).

The photograph in FIG. 1 shows the appearance of the obtained porous sheet ("sponge type LYDEX").

4) Observation of Porous Sheet Using a Stereomicroscope

Figure 2:
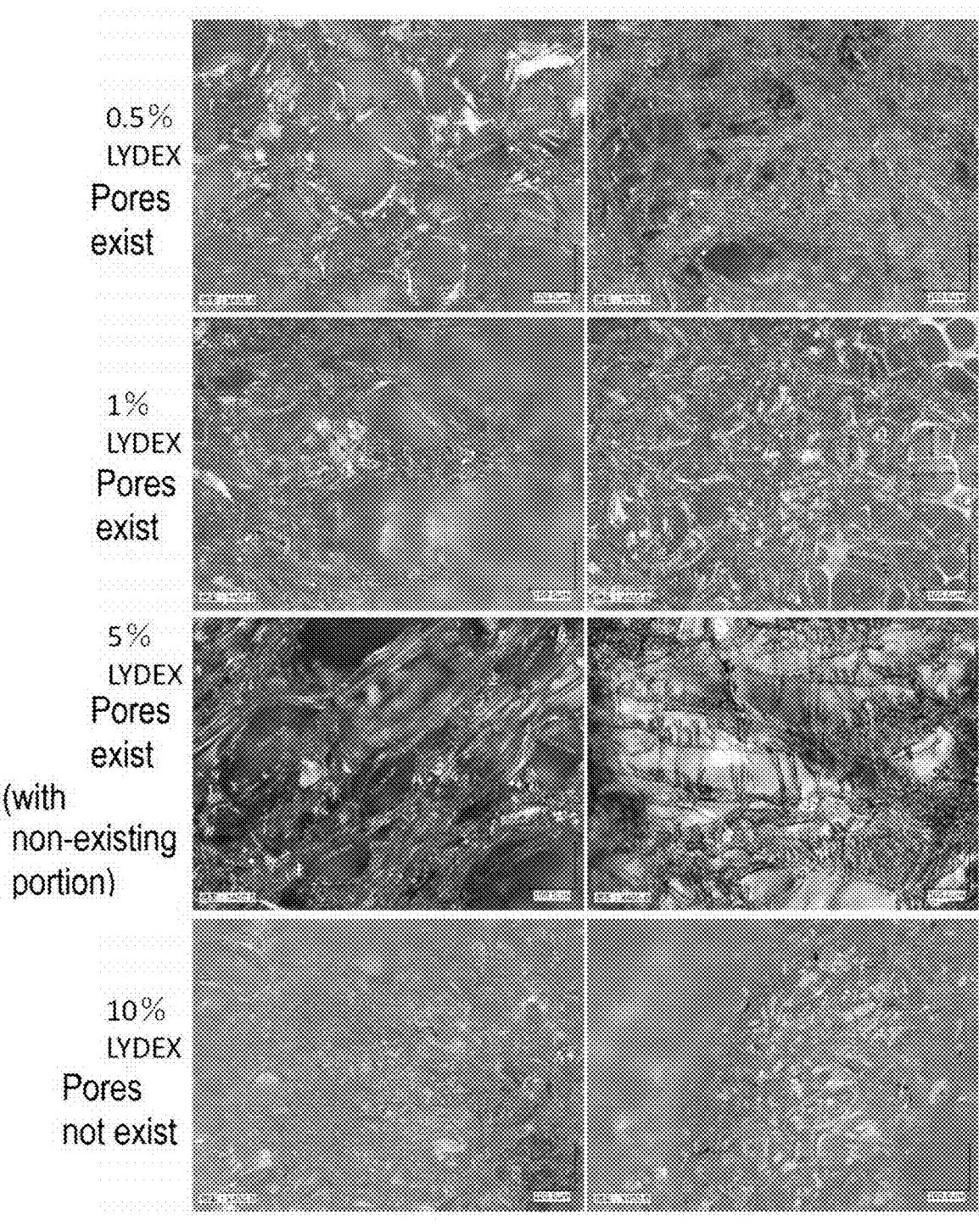
FIG. 2 shows a set of stereoscopic micrographs where concentrations of the suspensions during the gel formation reaction (SAPL concentration in Table 2) were set to 0.5%, 1%, 5%, and 10% (Example).

FIG. 2 shows photographs of a stereomicroscope (Keyence VHX-5000) when the concentration of the suspension during the gel formation reaction (SAPL concentration in Table 2) was set to four levels: 0.5%, 1%, 5%, and 10%, as presented together.

As is clear from FIG. 2, large-sized voids with a major axis diameter of 100 μm were not observed only when the concentration was 10%. Based on the results of such observations, porous sheets obtained at a concentration of 10% were used in experiments for ophthalmological treatments.

5) Trabeculectomy Using Rabbits

Figure 3:
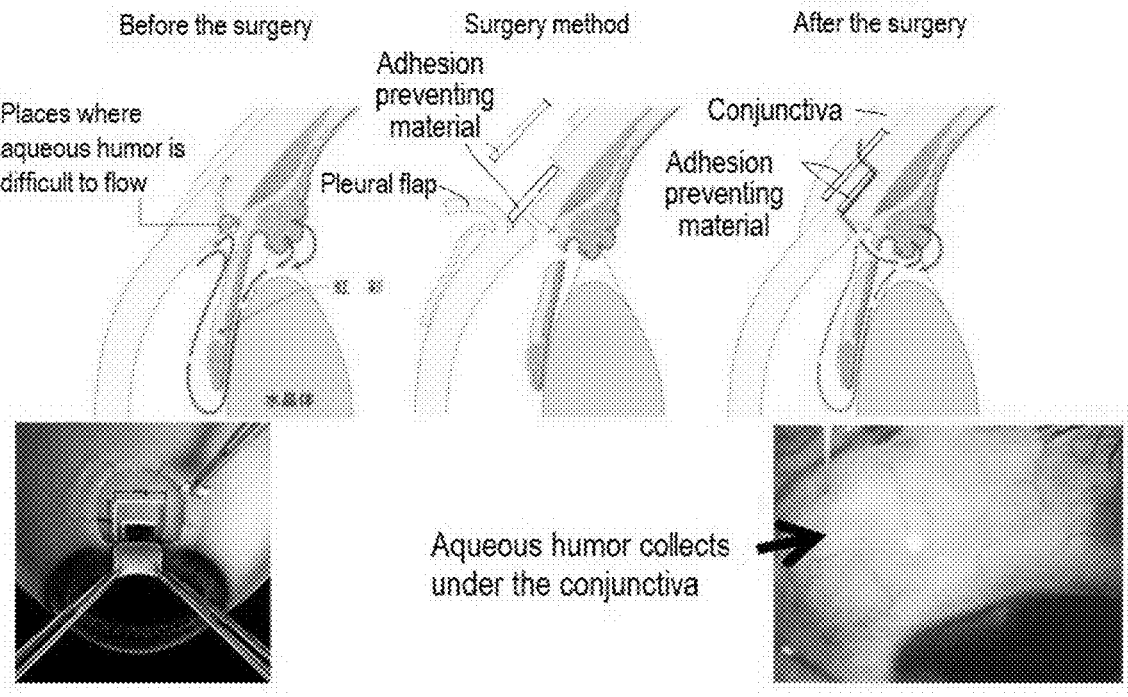
FIG. 3 shows a schematic view illustrating a procedure of the glaucoma surgery.

A surgery similar to above-mentioned glaucoma surgery was performed on a normal white rabbit. FIG. 3 schematically shows the main points of the surgery.

Adopted one for this surgery was the "sponge type LYDEX" of the Example obtained above (the amount of introduced aldehyde group in the first reactant was 0.44 to 0.48 mol/AGU, and the residual amino group ratio in the second reactant was 81% to 93%, the density when formed into a sheet was 10%, the height was 0.7 mm, and the thickness of the product was 0.4 mm); and the sheet was cut into a rectangle shape of approximately 1.5 mm×3 mm.

After forming the drainage channel as described above, a small piece of the porous sheet ("sponge type LYDEX") cut out as above was attached under the scleral flap and between the conjunctiva and the sclera. Then, the ends of the conjunctiva were sutured.

5-1) at the End of Surgery to Four Months after Surgery

Figure 4:
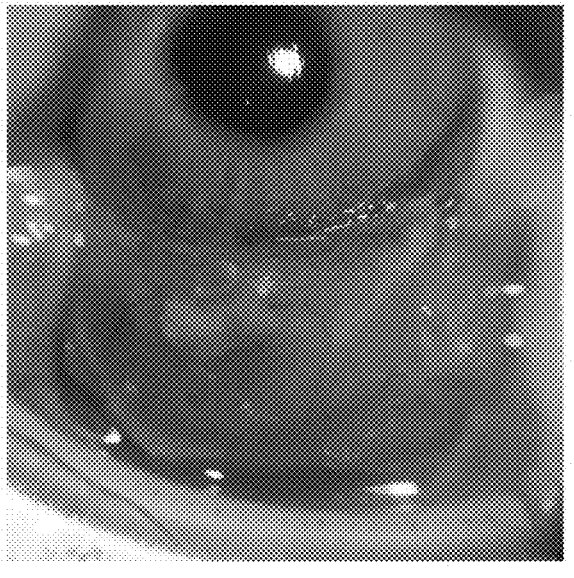
FIG. 4 shows photographs showing the appearance of a rabbit's eye immediately after the glaucoma surgery (trabeculectomy).
Figure 4:
Figure 5:
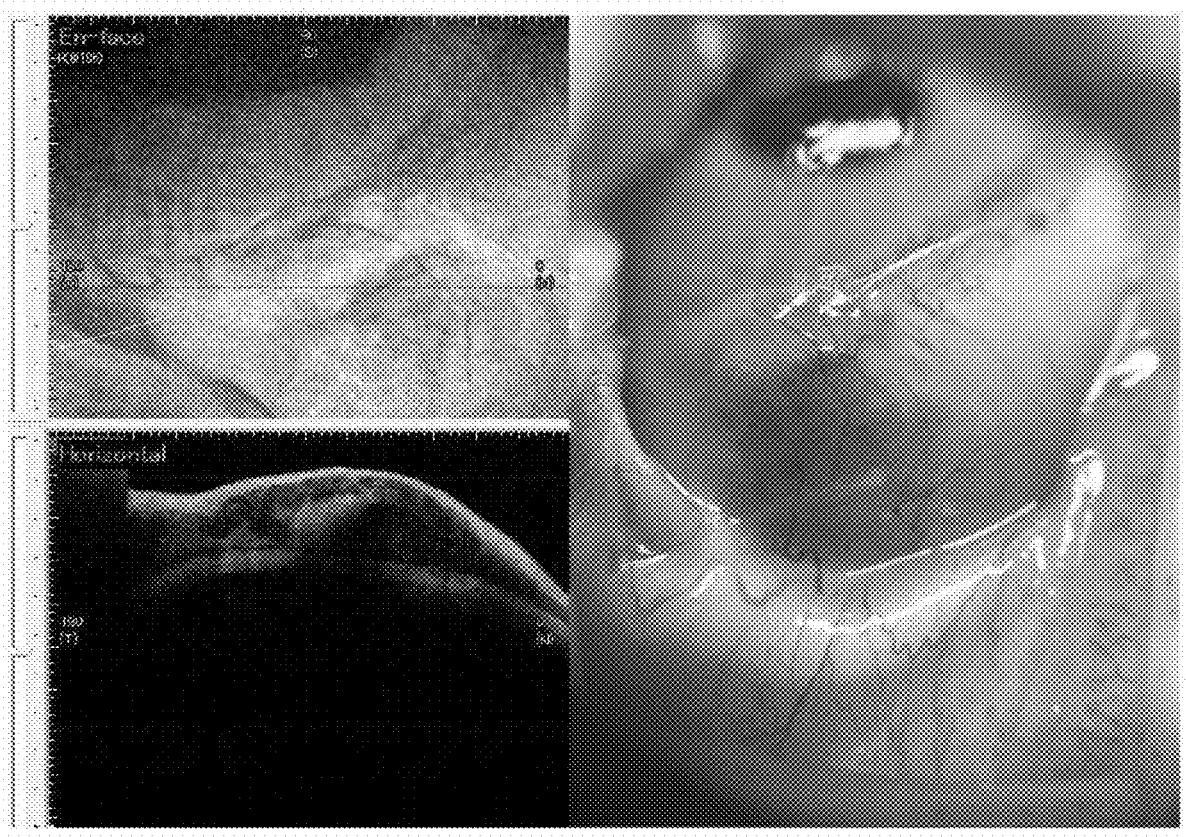
FIG. 5 shows photographs similar to FIG. 3 taken 4 weeks after the surgery.
Figure 6:
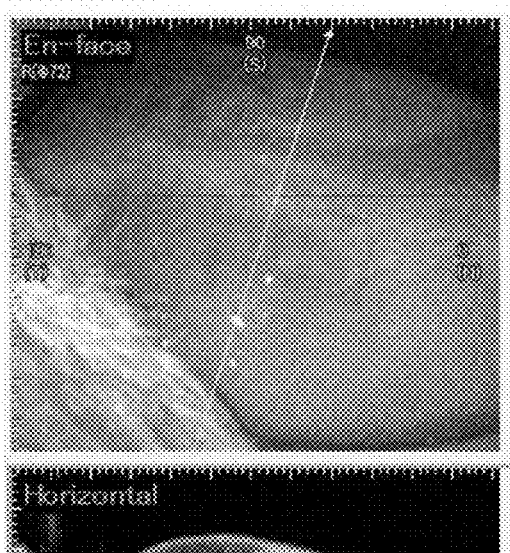
FIG. 6 shows photographs similar to FIG. 3 taken 4 months after the surgery.
Figure 6:
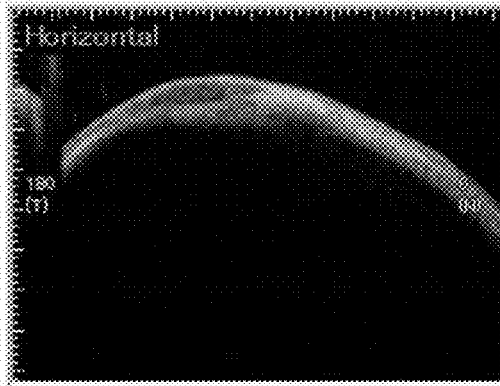
Figure 6:

The photograph in FIG. 4 shows a state at the end of the surgery, the photograph in FIG. 5 shows a state four weeks after the surgery, and the photograph in FIG. 6 shows the photograph four months after the surgery. As graspable from FIG. 5, after four weeks, the hydrogel of the adhesion prevention material remained at almost the same size as immediately after the surgery; and as graspable from FIG. 6, even after four months, the hydrogel of the adhesion preventing material was mostly remained.

Figure 7:
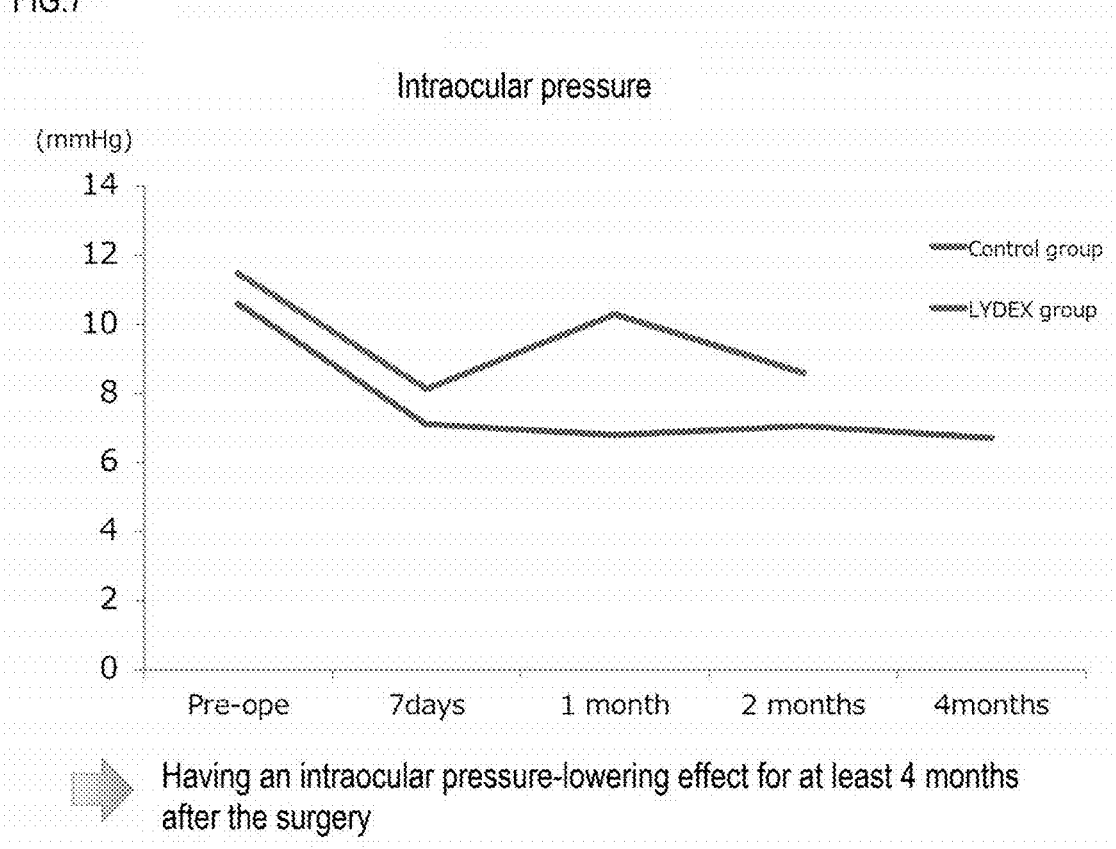
FIG. 7 shows a graph showing changes over time in intraocular pressure before and after surgery.

FIG. 7 shows changes in intraocular pressure over time. The reduction in intraocular pressure compared to that before the surgery ("pre-op") was maintained for four months. The control group in FIG. 7 shows the results when mycomycin C was used as conventional way without using the hydrogel of the embodiment, where the effect of lowering intraocular pressure was unstable.

Figure 8:
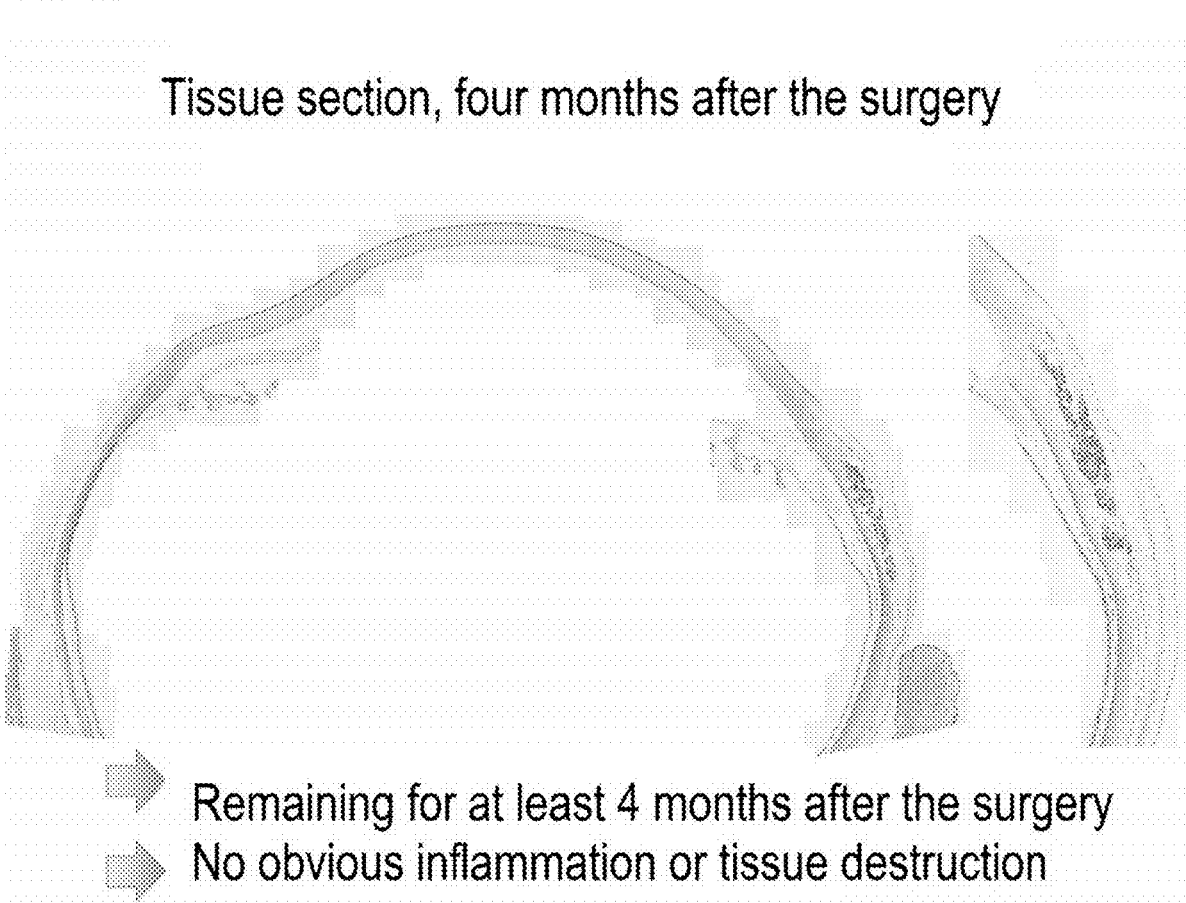
FIG. 8 shows an image of a cross-section of the eyeball, four months after surgery, as taken by CT photography and main parts are extracted into the image.

FIG. 8 shows a cross-section of the eyeball as taken by using CT photography, four months after the surgery, and then by extracting the peripheral areas of the eyeball. This also indicates that the hydrogel, which is an adhesion prevention material, remains in the predetermined location in a sufficient size, even after four months.

5-2) One Year and Nine Months after the Surgery

Figure 9:
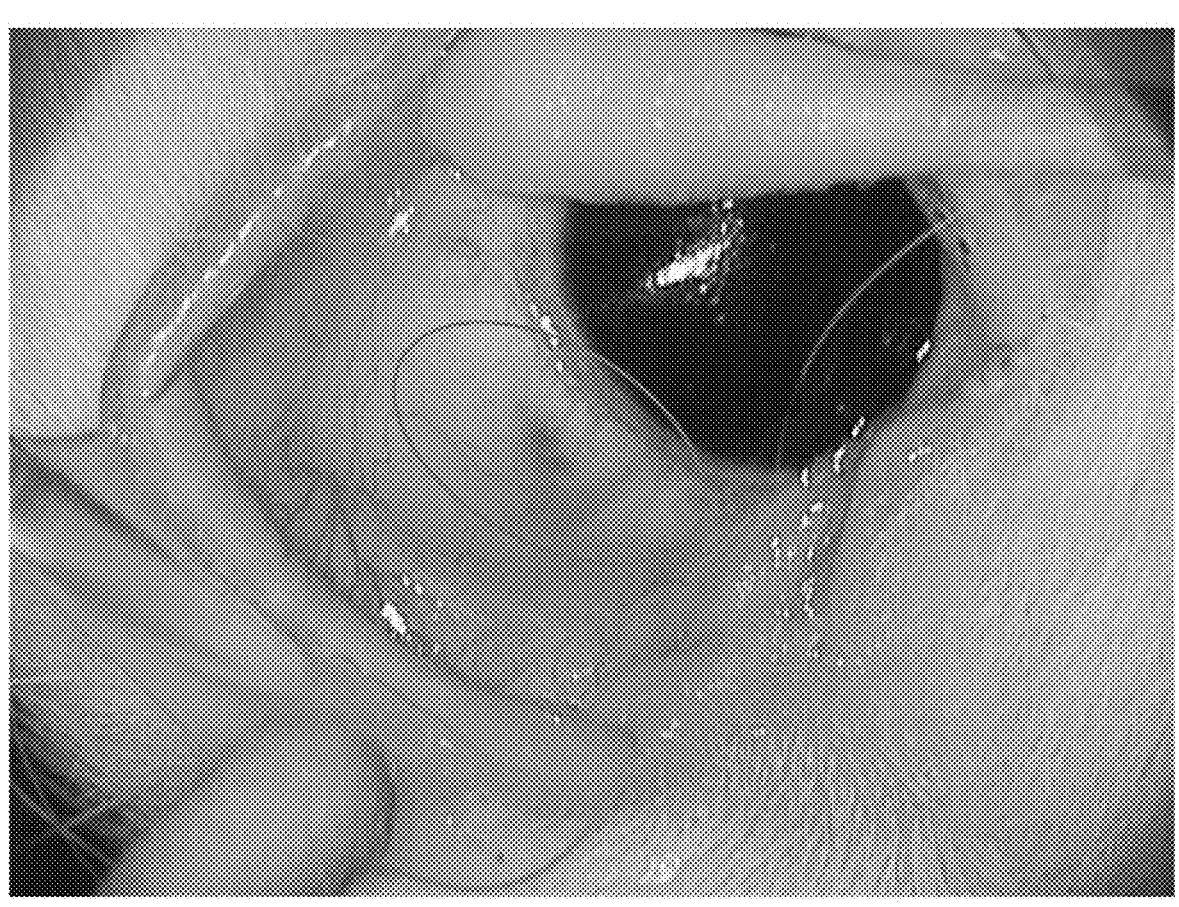
FIG. 9 shows a Photograph (1) confirming the outflow of blue dye from the surgical site one year and 9 months after the surgery.
Figure 10:
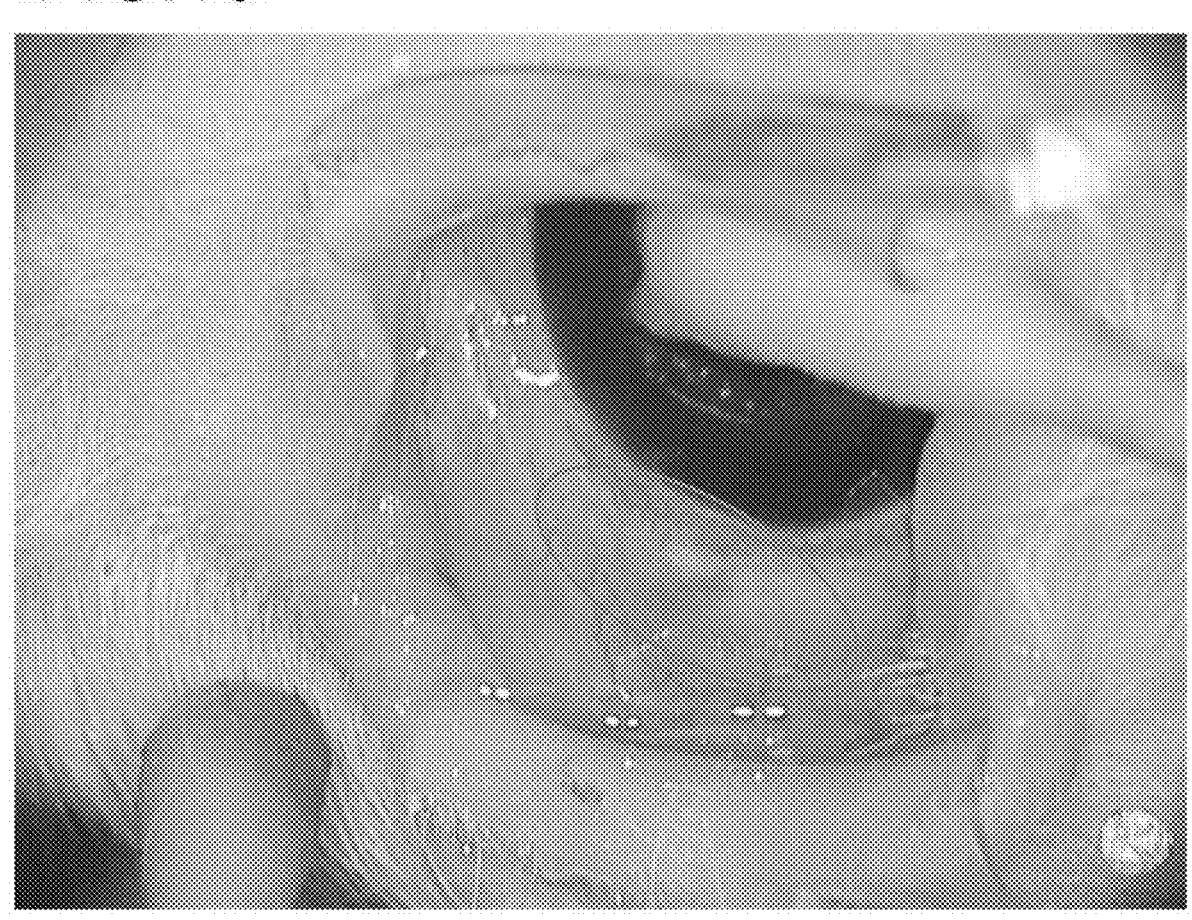
FIG. 10 shows a Photograph (2) confirming the outflow of blue dye from the surgical site one year and 9 months after the surgery.

Next, the photographs in FIGS. 9 and 10 show a state one year and nine months after the surgery. In these photographs, the surgical areas of the rabbit's left and right eyes are shown in the center of the oval markings. The surgical area was tinted as blue in the color photograph, but it appears as a "stain" in the grayscale photographs of FIGS. 9 and 10.

Here, in order to confirm whether the surgical part is functioning, that is, to confirm whether there is communication from the inside of the anterior chamber to the outside of the eye (from inside the anterior chamber to under the scleral flap→under the conjunctiva), a blue dye (trypan blue) was administered intracamerally. As a result, the outflow of blue pigment to outside the eye (under the flap) was confirmed within 15 to 60 minutes. Furthermore, no leakage to the subconjunctiva was confirmed. From this, it appears that at least the flap was functioning one year and nine months after the surgery.

The results of other measurements and observations at a time one year and nine months after the surgery are as follows.

Left and right intraocular pressure: 8 mmHg, and 9 mmHg

Conjunctival mobility: extremely good in both eyes

Anterior segment OCT: It was confirmed that there is space under the flap in both eyes and the area is not physically adhered.

From the above results, it was known that the effects of glaucoma surgery persisted for one year and nine months after the surgery.

Example 2

Table 4 below shows the results of evaluating the ease of handling when using the porous sheet for the trabeculectomy by changing the manufacturing conditions of the porous sheet, as shown in Table 3 below.

TABLE 3

| Lot No. | AD | SAPL | AD:SAPL | LYDEX concentration | Liquid volume | Size | Pressing |
|---|---|---|---|---|---|---|---|
| 1 | 2.5/20 | 1.0/10 | 4:1 | 1.0% | 10,000 mL | Large | Conducted |
| 2 | 2.5/20 | 1.0/10 | 4:1 | 1.0% | 3,000 mL | Small | Not conducted |
| 3 | 2.5/20 | 1.0/10 | 4:1 | 2.5% | 3,000 mL | Small | Not conducted |
| 4 | 2.5/20 | 1.0/10 | 4:1 | 4.0% | 3,000 mL | Small | Not conducted |
| 5 | 5.0/20 | 1.0/10 | 4:1 | 1.0% | 3,000 mL | Small | Not conducted |
| 6 | 2.5/20 | 1.0/10 | 4:1 | 0.5% | 10,000 mL | Large | Not conducted |

In Table 3 above, the items in the uppermost row are as follows.

"AD": The charging ratio of sodium periodate (NaIO$_4$) to dextran as in the left half of Table 1. "5.0/20" in Table 3 is the same as "2.5/10" in Table 1, and the amount of introduced aldehyde group (mol/AGU) is 0.25 to 0.27, which amount is just over half of the "5.0/10" used in the trabeculectomy of Example 1. Moreover, the amount of introduced aldehyde group (mol/AGU) of "2.5/20" in Table 3 is a little more than half of that where the amount of aldehyde group introduced (mol/AGU) is "2.5/10".

"SAPL": Charging ratio of succinic anhydride to polylysine, or "SA/PL" (succinic anhydride-to-polylysine) in the second column from the right end of Table 2. This is the same as "1.0/10" used in trabeculectomy in Example 1.

"AD:SAPL": Charging weight ratio at which the reaction molar ratio of aldehyde group-to-amino group becomes 1.0. The process is the same as the production of the porous sheet ("sponge type LYDEX") in Example 1.

"LYDEX concentration" and "liquid volume": The concentration of the two-reactant adhesive (LYDEX)" in the "LYDEX suspension" when manufacturing "sponge type LYDEX" as in "3)" above, and their amounts.

"Size": The diameter of the porous sheet is approximately 8.5 mm for "large" and approximately 3.6 mm for "small".

TABLE 4

| Lot No. | Thickness of the sheet | Ease of cutting the sheet | Degree of expansion when wet | Ease of tearing when wet | Subconjunctival inflammation (1 week) | Subconjunctival inflammation (1 month) | Conjunctival mobility (1 week) | Conjunctival mobility (1 month) |
|---|---|---|---|---|---|---|---|---|
| 1 | 1 | 5 | 1 | 3 | 4 | 5 | 5 | 5 |
| 2 | 0 | 5 | 0 | 2 | 4 | 5 | 5 | 5 |
| 3 | 3 | 5 | 3 | 3 | 4 | 5 | 5 | 5 |
| 4 | 1 | 5 | 1 | 3 | 4 | 5 | 5 | 5 |
| 5 | 1 | 5 | 1 | 2 | 4 | 5 | 5 | 5 |
| 6 | 0 | 5 | 0 | 2 | 4 | 5 | 5 | 5 |

The grading criteria in Table 4 are as follows.

Sheet thickness 0: Thin - - - 5: Thick

Ease of cutting the sheet 0: Difficult to handle - - - 5: Good

Degree of expansion when wet 0: None - - - 5: Maximum

Easy to tear when wet 0: Unable to grip - - - 5: Cannot tear

Subconjunctival inflammation (1 week) 0: Maximum - - - 5: None

Subconjunctival inflammation (1 month) 0: Maximum - - - 5: None

Conjunctival mobility (1 week) 0: No mobility - - - 5: Good

Conjunctival mobility (1 month) 0: No mobility - - - 5: Good

Although each of the porous sheets tested ("sponge type LYDEX") was adoptable, Lot No. 5 had a uniform density throughout the sheet, and was particularly easy to handle.

Example 3

A porous sheet was obtained in the same manner as in Example 1, except that glycerin (glycerol) was added to the mixed aqueous solution during the gelation reaction. Specifically, the porous sheet was obtained as follows.

The total solution volume was "height of 0.7 mm" X (multiplied by) "bottom area of a container made entirely of soft silicone"; and, amounts of the solutions were respectively calculated and the solutions were respectively weighed so as to achieve the following ratio: first reactant solution (AD-aq)/second reactant solution (ASAPL-aq)/glycerol=42.5/42.5/15. Firstly, the aldehyde solution (AD-aq) and glycerin were added to the container and stirred thoroughly using a tool such as a spatula. Subsequently, the succinic anhydride-added poly-L-lysine (SAPL-aq) was added and mixed in the same way; and then the mixture became viscous. At this stage, the mixed solution was spread over the entire bottom of the container and allowed to stand at room temperature for about 10 minutes to form a gel. After visually confirming gelation, the entire container was dried in a vacuum dryer. The temperature-setting at this time is preferably 30° C. or less. After drying, a film was removed from the container in a careful manner to avoid tearing of the film; and then, trimmed if necessary.

By producing the sheet with a liquid amount of 0.7 mm in height, a sheet having a thickness of approximately 0.4 mm was created. When forming the sheet having smaller thickness, smaller amount of the mixed liquid resulted in that the liquid would not be spread all over the bottom of the container.

Reference Example

A fine spherical (microbead-shaped) porous material was obtained using a procedure similar with above-mentioned porous material. Specifically, into a beaker, liquid paraffin containing 2% sorbitan monooleate is poured and stirred by using a stirring bar. Then, into the solution while being stirred, the "liquid LYDEX" (AD-aq and SAPL-aq) was dropped by a dual syringe at a rate that allows each drop to be visually observed. The size of the beads was adjusted by adjusting the stirring speed and dropping speed (the amount of one drop added). After dropping, the solution became cloudy. The solution was further stirred for at least 10 minutes even after it becomes cloudy. After being stirred, the mixture was allowed to stand overnight at room temperature or at 4° C., and the white cloudy precipitate and supernatant were separated. Then, thus separated supernatant was discarded; and the precipitate was added with acetone and stirred to give observable white particles. The particles in the supernatant were filtered through a mesh (of an arbitrary size) and collected together with the sediment at the bottom of the beaker; and the sediment was placed on a filter paper little by little and washed with acetone. Washing was performed by replacing the filter paper with a new one each time until the paraffin stain was removed from the filter paper. The resulting particles were dried until the acetone evaporates to give microbead-shaped "LYDEX". Thus obtained porous bodies were all approximately spherical and had a diameter of approximately 10 to 30 μm.

Microbead-shaped porous material was injectable into the surgical site using a syringe while the porous material was difficult to be secured at a predetermined site because the porous material do not have adhesive (sticky) properties. Microbead-shaped porous materials seemed to be usable when combined with network-shaped porous materials, block-shaped hydrogels, etc.

What is claim is:

1. An ophthalmic adhesion inhibiting material for ophthalmology, which is a continuous-pore porous sheet comprising a resin material formed by reaction product of:

an aldehyde glycan as a first reactant, which has a weight average molecular weight of 10,000 to 5 million, and an introduced aldehyde groups amount per anhydroglucose unit (mol/AGU) of 0.4 to 0.7; and a carboxylic anhydride-added poly-L-lysine as a second reactant, having a weight average molecular weight of 1000 to 100,000 and a residual amino groups ratio of 80 to 99%; wherein reaction molar ratio of aldehyde group to amino group is 0.9 to 1.1;

apparent density (bulk density) is from 0.1 to 0.25 g/cm³; and thickness is from 0.1 to 0.8 mm.

2. The ophthalmic adhesion inhibiting material for ophthalmology according to claim 1, wherein the resin material contains a moisture-retaining plasticizer comprising glycerin or a water-soluble low-molecular compound, in an amount of 30 to 100% by weight or 50 to 90% by weight, based on total weight of the first reactant and the second reactant.

3. The ophthalmic adhesion inhibiting material for ophthalmology according to claim 1, which has no voids having a major axis diameter of 80 μm or more when the surface or cut surface is observed with a stereoscopic microscope.

4. The ophthalmic adhesion inhibiting material according to claim 1, which is used for glaucoma surgery.

5. A method for producing the ophthalmic adhesion inhibiting material according to claim 1, comprising:

mixing and reacting the first reactant and the second reactant in presence of water, wherein concentration of the resin material becomes 8 to 20%; and freeze-drying a hydrogel obtained by the reacting or suspension before gelation so as to obtain the porous sheet.

* * * * *